United States Patent [19]
Manz et al.

[11] Patent Number: 5,371,019
[45] Date of Patent: Dec. 6, 1994

[54] METHOD AND APPARATUS FOR ANALYZING REFRIGERANT PROPERTIES

[75] Inventors: Kenneth W. Manz, Paulding; Sandra Snyder, Bryan, both of Ohio

[73] Assignee: SPX Corporation, Muskegon, Mich.

[21] Appl. No.: 160,224

[22] Filed: Dec. 2, 1993

[51] Int. Cl.$^5$ .......................... G01N 33/00; F25J 3/00; F25B 49/00
[52] U.S. Cl. .................................... 436/126; 436/164; 436/171; 422/82.05; 62/37; 62/125; 62/127
[58] Field of Search .......................... 436/126, 164, 171; 422/82.05; 62/125, 127, 37

[56] References Cited

U.S. PATENT DOCUMENTS

| | | | |
|---|---|---|---|
| 4,436,641 | 3/1984 | Stelz et al. | 252/68 |
| 4,809,520 | 3/1989 | Manz et al. | 62/292 |
| 4,862,699 | 9/1989 | Lounis | 62/84 |
| 4,923,806 | 5/1990 | Klodowski | 436/39 |
| 4,942,134 | 7/1990 | Winefordner et al. | 436/161 |
| 5,062,273 | 11/1991 | Lee et al. | 62/85 |
| 5,158,747 | 10/1992 | Manz et al. | 422/98 |
| 5,174,124 | 12/1992 | Paige et al. | 62/125 |
| 5,237,873 | 8/1993 | Eichenlaub | 73/597 |
| 5,247,804 | 9/1993 | Paige et al. | 62/77 |
| 5,255,527 | 10/1993 | Paige | 62/85 |

*Primary Examiner*—Nina Bhat
*Attorney, Agent, or Firm*—Barnes, Kisselle, Raisch, Choate, Whittemore & Hulbert

[57] ABSTRACT

One or more properties of a refrigerant are analyzed by evacuating a refrigerant sample vessel, drawing a refrigerant vapor sample into the vessel, and condensing the refrigerant sample within the vessel for measurement and indication of one or more desired properties of the liquid refrigerant sample. By drawing the sample refrigerant in vapor phase rather than liquid phase, the sample will be relatively free of lubricant, particulate or water contamination. The sample vessel can be readily cleaned by simple evacuation in preparation for the next measurement cycle.

11 Claims, 3 Drawing Sheets

METHOD AND APPARATUS FOR ANALYZING REFRIGERANT PROPERTIES

The present invention is directed to refrigerant handling systems, and more particularly to a method and apparatus for analyzing properties of refrigerants such as refrigerant make-up or composition.

BACKGROUND AND OBJECTS OF THE INVENTION

It is now widely recognized and accepted that release into the atmosphere of chlorofluorocarbon(CFC)-based and hydrochlorofluorocarbon(HCFC)-based refrigerants has a deleterious effect on the ozone layer that surrounds the earth. Production of CFC-based and HCFC-based refrigerants are to be severely curtailed in the future, and the cost of refrigerant for service purposes is already increasing. It has therefore become standard practice in the refrigeration system service industry to recover, recycle and reuse the refrigerant in the refrigeration system under service, or to recover, store and reclaim the refrigerant for later reuse, rather than merely to vent such refrigerant into the atmosphere and replace with new refrigerant as has been common practice in the past. U.S. Pat. Nos. 4,768,347, 4,805,416 and 4,878,356, all assigned to the assignee hereof, disclose equipment for recovering, recycling and/or recharging refrigerant in a refrigeration system service environment.

As currently envisioned R12 refrigerant is being replaced by different types of refrigerants in production of new refrigeration systems. For example, R12 refrigerant is being replaced by R134a refrigerant in the automotive industry—i.e., in automotive air conditioning systems. However, because these refrigerants and their associated lubricants are chemically incompatible with each other, inadvertent mixture of even small amounts of the different refrigerants can cause severe damage and early failure of the refrigeration system. It has been proposed to provide different service fittings on refrigeration equipment using different types of refrigerants, but the use of adapters and the like in the service industry may still result in inadvertent mixing of refrigerant-/lubricant types, with consequent damage to the system under service and to the service equipment itself. A further complication arises with the use of intermediate refrigerants as substitutes for R12 refrigerant, such as ternary blends made by DuPont. With severe curtailment of R12 production in the future, it is anticipated that a significant number of refrigeration systems currently employing R12 refrigerant may eventually be retro-fitted with an intermediate substitute refrigerant. Inadvertent mixing of refrigerants is considered to be an irreversible process, leading to disposal of the mixed refrigerant as hazardous waste.

The various types of refrigerants therefore need to be kept separate to protect the integrity of the service equipment, and to ensure proper integrity and performance of the refrigeration equipment under service. Use of an incorrect refrigerant or an undesired mixture of refrigerants can occur due to improperly charging the incorrect refrigerant into the refrigeration equipment during installation or service, selective leakage or purging of one refrigerant component in a non-azeotropic refrigerant mixture, incomplete removal of the previous refrigerant in retro-fitting equipment or clearing of the recovery/recycling service system, chemical reaction within the refrigerant such as during a high temperature mechanical failure or hermetic compressor burnout generating undesirable refrigerant byproducts, or inadvertent mixing by recovery of refrigerant into an incorrect container or incorrect consolidation of recovered refrigerants into a larger container for shipment to a reclaim processing center.

In the past, refrigerant analysis has been accomplished by drawing a liquid refrigerant sample and sending the sample to a fully equipped refrigerant chemistry laboratory. An experienced chemist can remove some contaminants, such as oil, water and metallic particles, and then analyze the refrigerant using gas chromatography, mass spectroscopy or infrared spectroscopy. Air-Conditioning and Refrigeration Institute Standard 700-88 Specifications for Fluorocarbon Refrigerants specifies analysis of a liquid refrigerant sample. However, such laboratory analysis requires several hours or days to obtain, and is thus not suitable for use in the field. There is therefore a need in the refrigeration system service industry for a device that can be employed to test refrigerant in a storage container, or in a refrigeration system before performing service on the system, that is not restricted to any particular type of refrigerant or to automotive service applications, that is particularly well adapted to identify and distinguish between refrigerants of different types, that is inexpensive to manufacture and market, that is readily portable, that is rapid and efficient in operation, and/or that can be employed by relatively untrained service personnel.

U.S. Pat. No. 5,158,747 assigned to the assignee hereof discloses a device for identifying and distinguishing between and among refrigerants of different types. The device includes a fixed volume for containing a sample of refrigerant. The refrigerant to be tested is selectively admitted into the volume in vapor phase, vapor pressure of refrigerant within the fixed volume is measured, and admission of refrigerant is terminated when the vapor pressure of refrigerant contained in the volume reaches a preselected level. A sensor and associated electronics are coupled to the sample-containing volume for determining type of refrigerant vapor as a function of one or more selected properties of the refrigerant, and indicating such refrigerant type to an operator. U.S. application Ser. No. 08/047,263, also assigned to the assignee hereof, discloses an improved apparatus in which a thermistor provides a first electrical signal as a function of the combined effect of thermal conductivity and temperature of a refrigerant vapor sample in the sample-containing volume, and a temperature sensor provides a second electrical signal as a function of temperature of the refrigerant vapor sample essentially independent of thermal conductivity. Associated electronics determine type of refrigerant in the sample-containing volume as a function of the first and second electrical signals, and thus as a function of thermal conductivity of the refrigerant sample independent of sample temperature.

It has heretofore been proposed to employ near-infrared spectrophotometric analysis techniques for determining refrigerant make-up or composition. A liquid phase refrigerant sample is fed to a boiler, where the refrigerant sample is vaporized to separate refrigerant from oil and water. The refrigerant vapor is fed to a sample cell, where the vapor is condensed and subjected to near-infrared spectrophotometric analysis. Refrigerant make-up (i.e., refrigerant type or mixture of types) is determined by comparison of the near-infrared absorption spectra of the sample with prestored spectral data representative of known refrigerant types. Although the technique so proposed can provide an accurate indication of refrigerant type or types, improvements remain desirable. In particular, simplification is desirable to adapt the technique for use in the field. For example, the liquid phase refrigerant sample can contain up to twenty percent lubricant as well as dirt and metal particles, which can affect precision of the measurement process. The possible introduction of lubricant and particulates also necessitates cleaning of the test chamber or cell between uses.

SUMMARY OF THE INVENTION

In accordance with one aspect of the present invention, one or more properties of a refrigerant are analyzed by evacuating a refrigerant sample vessel, drawing a sample of refrigerant vapor into the vessel, and condensing the refrigerant sample within the vessel for measurement and indication of one or more desired properties of the liquid refrigerant sample. By drawing the sample refrigerant in vapor phase rather than liquid phase as heretofore proposed, the sample will be relatively free of lubricant, particulate and water contamination. The sample cell can be readily cleaned by simple evacuation in preparation for the next measurement cycle. Furthermore, the method and apparatus are greatly simplified by eliminating the necessity for boiling a liquid refrigerant sample.

The sample vessel may be evacuated preparatory to drawing a vapor refrigerant sample by connecting the vessel to a vacuum pump, or by connecting the vessel through an evaporator to a compressor in a refrigerant handling system. In either case, the sample vessel is evacuated to remove the prior refrigerant sample and any contaminants to a preferred vacuum level of at least 5000 micrometers of mercury absolute, and more preferably to a vacuum level of at least 500 micrometers of mercury absolute. When the sample vessel is then connected to a source of refrigerant in vapor phase, such as the vapor port of a refrigerant storage container or a refrigeration system, reduced pressure in the sample vessel functions automatically to draw a refrigerant sample into the vessel. The refrigerant sample may be condensed in the vessel by reducing temperature within the vessel after the sample has been drawn, or by reducing temperature within the vessel prior to drawing the refrigerant sample. The latter alternative has the advantage of assisting the reduced pressure within the sample vessel in drawing the refrigerant sample, and in helping to fill the vessel with a stable sample of liquid phase refrigerant. Temperature conditions within the sample vessel should then be maintained at a constant level to promote stability of the liquid refrigerant sample during the measurement process.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENTS

Figure 1:
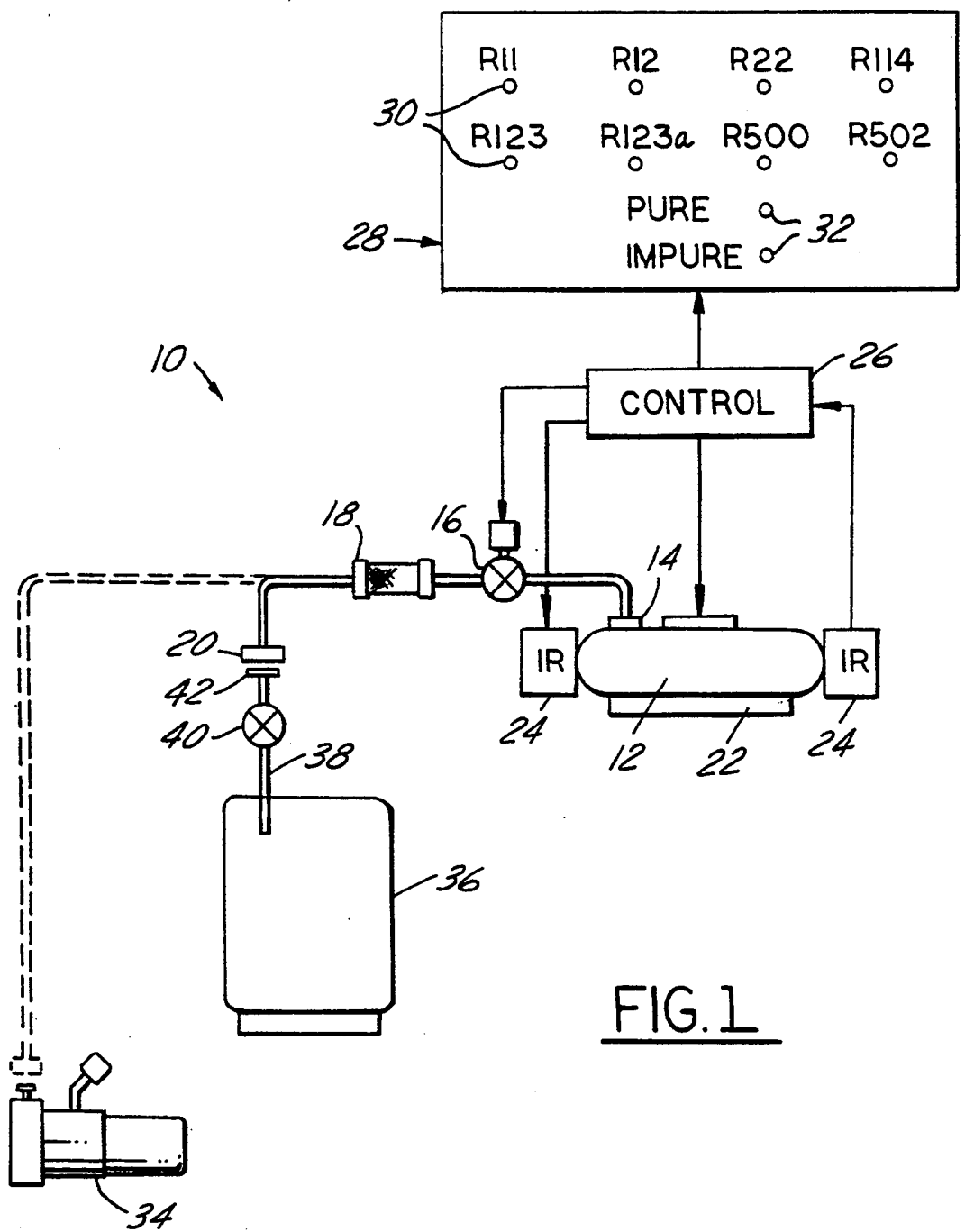
FIG. 1 is a schematic diagram of a refrigerant analysis apparatus in accordance with one presently preferred embodiment of the invention.

FIG. 1 illustrates an apparatus 10 for analyzing refrigerant in accordance with one presently preferred embodiment of the invention as comprising a vessel or cell 12 for receiving and holding a refrigerant sample. Vessel 12 has an inlet fitting 14 at one end connected through a solenoid valve 16 and a filter 18 to a coupling 20 for connection to a source of refrigerant vapor. Filter 18 may be of any suitable conventional type for removing particles and/or water from refrigerant vapor flowing therethrough. Coupling 20 preferably comprises a self-sealing quick-disconnect coupling such as illustrated, for example, in U.S. Pat. No. 5,080,132 and U.S. application Ser. No. 07/862,209. A thermoelectric heater/cooler 22 surrounds and is in heat conductive contact with the outer wall of vessel 12. A sensor 24 is also coupled to vessel 12 for measuring one or more properties of refrigerant contained therewithin. Preferably, sensor 24 comprises a source of near-infrared light and suitable filter/sensor units for illuminating refrigerant within vessel 12 and obtaining spectrophotometric absorption data as a function of wavelength.

Heater/cooler 22, sensor 24 and solenoid valve 16 are connected to an electronic control unit 26, which also drives a display 28 for indicating one or more measured properties of the refrigerant under test. That is, display 28 includes a plurality of lamps 30 disposed adjacent to associated printed indicia for indicating refrigerant type—e.g., R11, R12, R22, R114, R123, R123a, R500 and R502. A second pair of lamps 32 are disposed adjacent to respective printed indicia on display 26 for indicating either "pure" or "impure" condition of the refrigerant, depending upon whether the refrigerant is contaminated with other refrigerants, or is ready for reuse.

In operation, sample vessel 12 is first evacuated. This may be accomplished by connecting the vessel through coupling 20 to a vacuum pump 34, opening valve 16 through control 26, and then operating the vacuum pump to draw a vacuum (i.e., sub-atmospheric pressure) within the vessel. Preferably, pressure within the vessel is reduced below at least 5000 micrometers, and most preferably below 500 micrometers of mercury absolute, in order to ensure that the prior refrigerant sample and all contaminants are removed from within the vessel. Vaporization and evacuation of the prior refrigerant sample may be assisted by energizing thermoelectric heater/cooler 22, using control 26, to vaporize the refrigerant sample. With valve 16 then closed, coupling 20 is removed from vacuum pump 34 and fastened to a source of test refrigerant vapor. In FIG. 1, this source is illustrated as a refrigerant storage container 36 having a vapor port 38 connected through a manual valve 40 to a fitting 42 that mates with coupling 20. In this configuration, apparatus 10 is used to analyze refrigerant within storage container 36. The apparatus may also be employed to analyze refrigerant within a refrigeration system under service, for example, by connecting coupling 20 to the system vapor port and opening the associated valve, if any.

In any event, with coupling 20 connected to fitting 42, valve 40 on container 36 is opened, and solenoid valve 16 is opened by control 26. Refrigerant vapor is drawn from within storage container 36 into vessel 12 by the reduced pressure within the sample vessel resulting from the prior evacuation process. In order to provide the desired liquid refrigerant phase for test purposes, the refrigerant vapor is condensed within vessel 12 by control circuit 26 operating heater/cooler 22 to cool the sample volume. This may be accomplished after drawing the refrigerant vapor sample from container 36, or vessel 12 may be precooled by heater/cooler 22 which not only assists the reduced pressure within vessel 12 in drawing refrigerant from container 36, but also condenses the refrigerant as it is drawn into vessel 12 and thereby helps increase filling of the vessel. If desired, transfer of refrigerant vapor to vessel 12 can be further enhanced by heating container 36 and thereby increasing vapor pressure of refrigerant contained therewithin. By drawing a vapor sample from source/container 36, inclusion of oil and/or water dissolved or suspended in the liquid refrigerant within the container will be greatly reduced.

With a liquid refrigerant sample now contained within vessel 12, infrared sensor 24 is then operated by control 26 for measuring one or more properties of the refrigerant. Sensor 24 may be of any suitable conventional type for obtaining absorption data from the refrigerant sample, which data is then compared in control electronics 26 to prestored absorption data from known refrigerant types. Such absorption data comparison shows not only the type of refrigerant within the vessel, but also whether the refrigerant sample is a mix of refrigerant types and whether the sample contains impurities (e.g., other refrigerants) that call for recycling or reclamation. Refrigerant type and purity so determined are indicated at display 28. Preferably, heater/cooler 22 is operated by control 26 to maintain temperature within vessel 12 substantially constant during operation of sensor 24. Most or all of the refrigerant sample may then be removed from vessel 12 by opening valve 16 and operating heater/cooler 22 in a heating mode, which transfers a major portion of the refrigerant sample back to vessel 36. Any refrigerant or contaminants remaining in vessel 12 will be removed by subsequent connection to vacuum pump 34 during the next sample/measurement cycle. Sensors 24 other than an infrared sensor, such as an x-ray diffraction sensor, may also be employed.

Figure 2:
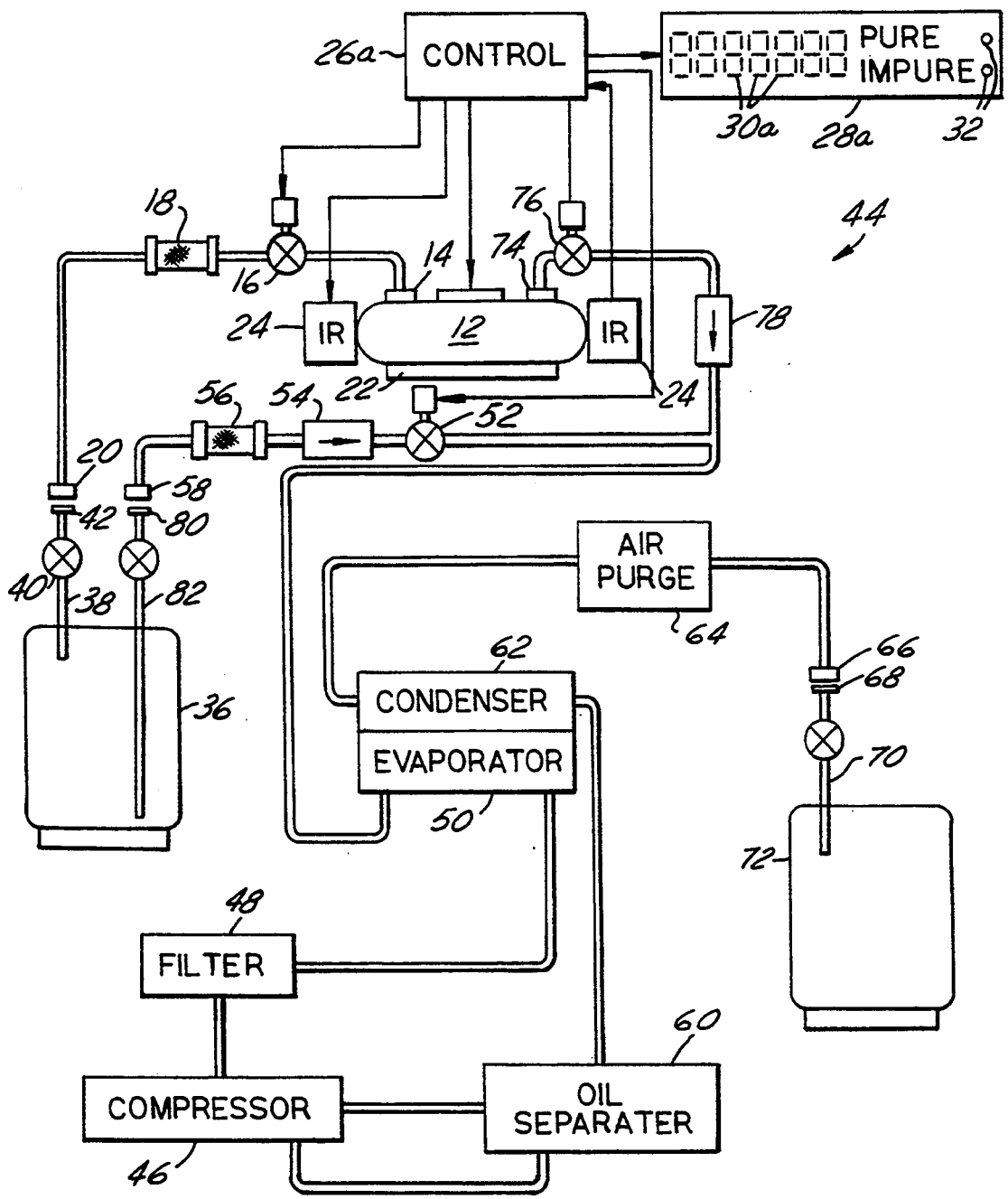
FIG. 2 is a schematic diagram of a refrigerant handling system that includes refrigerant analysis apparatus in accordance with a second embodiment of the invention.

FIG. 2 illustrates an analyzer in accordance with the invention embodied in a refrigerant recovery/recycling system 44. Reference numerals identical to those employed in connection with FIG. 1 indicate identical elements, and reference numerals followed by a suffix indicate modified but similar elements. Recovery/recycling system 44 includes a refrigerant compressor 46 having an inlet connected to a refrigerant evaporator 50 through a filter/dryer 48. Evaporator 50 is connected to an input coupling 58 through a solenoid valve 52, a check valve 54 and a particulate/water filter 56. The outlet of compressor 46 is connected to a compressor oil separator 60, which returns oil to the sump of compressor 46 and feeds refrigerant to a condenser 62. The outlet of condenser 62 is connected through an air purge arrangement 64 and a coupling 66 to a fitting 68 on the vapor port 70 of a refrigerant storage vessel 72. Vessel 72 has a fitting 74 connected to evaporator 50 through a solenoid valve 76 and a check valve 78 in parallel with the input line from solenoid valve 52. Input coupling 58 is connectable to a fitting 80 on the liquid port 82 of refrigerant storage container 36. Display 28a has four seven-segment alphanumeric characters 30a for indicating refrigerant type, and pure/impure indicators In operation, couplings 20,58 are connected to the vapor and liquid ports of vessel 36 (or the vapor and liquid ports of another refrigerant source). Control electronics 26a then functions in a first mode of operation for evacuating vessel 12 by closing valves 16,52, opening valve 76 and then operating compressor 46 to evacuate the sample containment vessel. When pressure within the vessel is below the desired evacuation level, which may be indicated by a suitable pressure sensor not shown, valve 76 is closed and compressor 46 is turned off. Valve 16 is then opened in a second mode of operation for admitting a refrigerant vapor sample into vessel 12. Vessel 12 is cooled by heater/cooler 22 either prior to or following admission of the refrigerant vapor sample as discussed above. The liquified refrigerant sample is then analyzed by sensor 24 and control 26a, with the results being indicated at display 28a as described above. If the analysis indicates that the refrigerant is of a type and/or purity suitable for transfer to container 72, valve 16 is closed, valve 76 remains closed, and valve 52 is opened in a third mode of operation in which compressor 46 is operated to transfer refrigerant from container 36 to container 72. In this refrigerant recovery/recycle transfer mode of operation, system 14 operates in the usual and conventional manner described in detail in the patents noted hereinabove. Following refrigerant transfer, solenoid valve 52 is closed and solenoid valve 76 is opened so that compressor 46 functions to evacuate the refrigerant sample from within vessel 12 and transfer the same to container 72.

Figure 3:
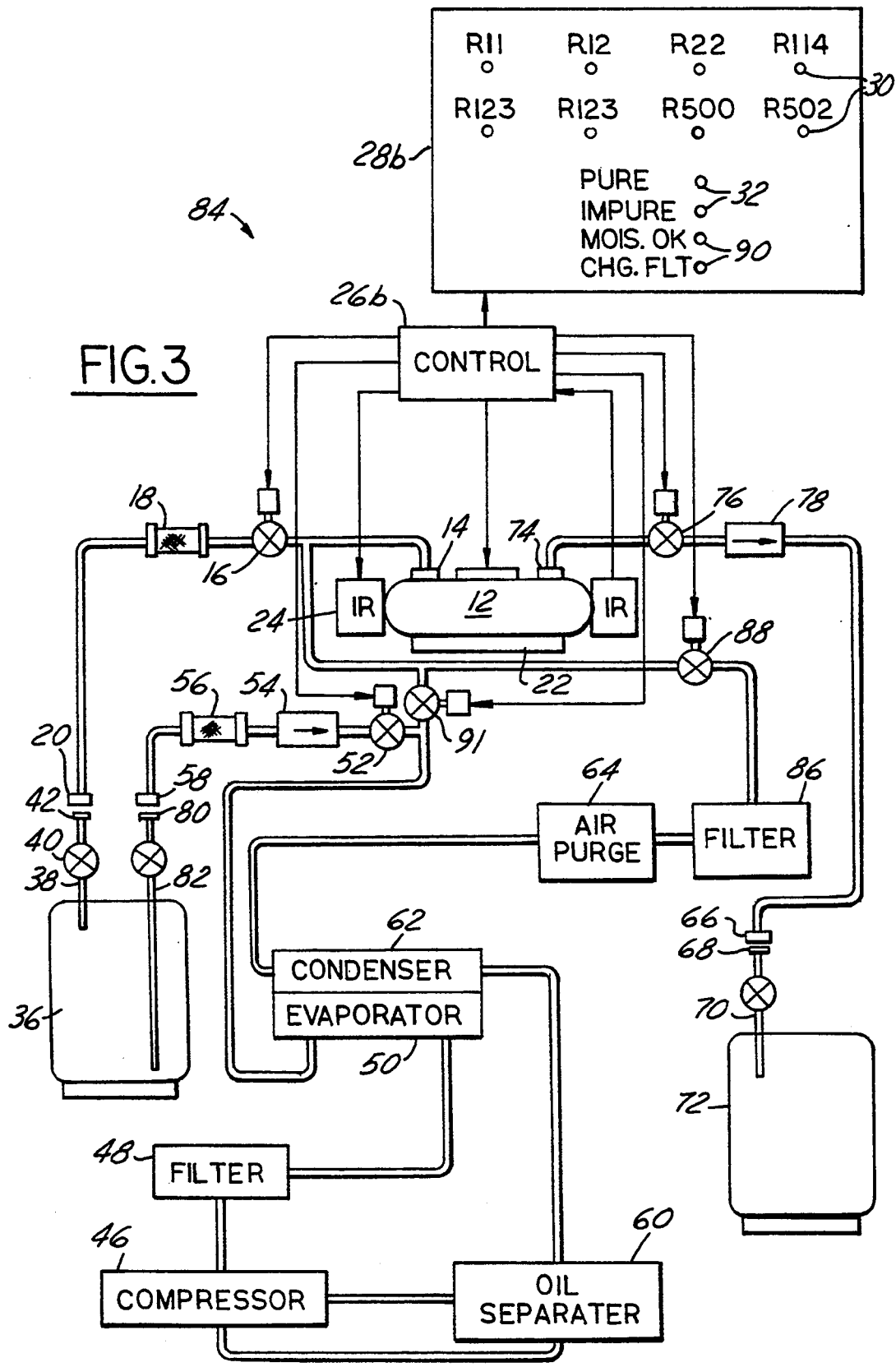
FIG. 3 is a schematic diagram that illustrates a modification to the system of FIG. 2 in accordance with a third embodiment of the invention.

FIG. 3 illustrates a modified refrigerant recovery/recycling system 84 in which refrigerant vessel 12 is connected downstream of condenser 62, air purge arrangement 64 and a second filter/dryer 86 for continuously monitoring refrigerant properties (e.g., Purity) during the recovery/transfer operation. That is, vessel fitting 74 is connected in the embodiment of FIG. 3 through solenoid valve 76 and check valve 78 to coupling 66 and fitting 68 on vapor port 70 of storage container 72. Filter 86 is connected through a solenoid valve 88 between sample inlet control valve 16 and vessel inlet fitting 14. A control valve 91 is connected between vessel inlet fitting 14 and the inlet side of evaporator 50. In operation, control 26b closes valves 16,76 and 52, and opens valves 88,90 to evacuate vessel 12 through operation of compressor 46. Valves 88,90 are then closed, and valve 16 is opened so that the reduced pressure within vessel 12 draws a refrigerant vapor sample from container 36. Valve 16 is then closed and the liquified refrigerant sample is analyzed as described above. If the sample is of the desired type and/or purity, valves 52,88 and 76 are opened, and compressor 46 is operated in the usual manner to draw refrigerant from container 36 and pump such refrigerant to container 72. The refrigerant flowing from condenser 62 flows through analysis vessel where the same is subjected to continuous analysis for moisture content. The result of such analysis is indicated at display 26b, which includes a pair of lamps 90 adjacent to printed indicia for indicating either that the moisture content of the refrigerant is satisfactory, or that a filter/dryer core change is required.

We claim:

1. A method of analyzing refrigerants for recovery and reuse that comprises the steps of:

(a) providing means for containing a refrigerant sample,
(b) drawing a vacuum in said means,
(c) drawing into said means a refrigerant sample in vapor phase for analysis and condensing the sample within said means to liquid phase,
(d) detecting composition, purity, or both composition and purity of the refrigerant in said means while said refrigerant is in liquid phase, and
(e) identifying said composition, purity or both composition and purity detected measured in said step (d).

2. The method set forth in claim 1 wherein said step (c) is accomplished by connecting said means to a source of refrigerant in vapor phase, such that the vacuum drawn in said means in said step (b) automatically functions to draw refrigerant from said source into said means.

3. The method set forth in claim 2 wherein the sample is condensed in said step (c) by reducing temperature within said means.

4. The method set forth in claim 3 wherein the step of reducing temperature within said means is carried out after the refrigerant sample is drawn into said means.

5. The method set forth in claim 3 wherein the step of reducing temperature within said means is carried out prior to the step of connecting said means to the refrigerant source, such that the refrigerant sample is at least partially condensed as it is drawn into said means from said source.

6. The method set forth in claim 1 wherein said step (d) is accomplished by subjecting the refrigerant sample in said means to near-infrared spectrophotometric analysis.

7. The method set forth in claim 1 wherein said step (b) is accomplished by connecting said means to a vacuum pump and operating said pump to draw a vacuum in said means.

8. The method set forth in claim 1 wherein said step (b) is accomplished by connecting said means to a compressor through means for vaporizing refrigerant, and operating said compressor to draw refrigerant from said means through said vaporizing means.

9. Apparatus for analyzing composition, purity or both composition and purity of refrigerants for recovery and re-use that comprises:
a sample vessel,
means coupled to said vessel for evacuating said vessel,
means for selectively connecting said vessel to a source of refrigerant in vapor phase so as to draw a vapor phase refrigerant sample into said vessel,
means coupled to said vessel for condensing the vapor phase refrigerant in said vessel to liquid phase,
means operatively coupled to said vessel for measuring composition, purity or both composition and purity of a condensed refrigerant sample in said vessel, and
means responsive to said measuring means for indicating composition, purity or both of said sample.

10. The apparatus set forth in claim 9 wherein said evacuating means comprises a vacuum pump with means for connection to said vessel.

11. The apparatus set forth in claim 10 further comprising a refrigerant compressor including means for selectively coupling said compressor to said source to pump refrigerant from said source, and wherein said means for evacuating said vessel comprises means for selectively coupling said compressor to said vessel.

* * * * *